US00PP30865P2

(12) United States Plant Patent
Vieyra, Jr.

(10) Patent No.: US PP30,865 P2
(45) Date of Patent: Sep. 3, 2019

(54) CHERRY TREE NAMED 'VIEYRA'

(50) Latin Name: *Prunus avium*
Varietal Denomination: Vieyra

(71) Applicant: Gabriel Vieyra, Jr., Orondo, WA (US)

(72) Inventor: Gabriel Vieyra, Jr., Orondo, WA (US)

( * ) Notice: Subject to any disclaimer, the term of this patent is extended or adjusted under 35 U.S.C. 154(b) by 0 days.

(21) Appl. No.: 15/932,385

(22) Filed: Feb. 21, 2018

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 5/08; A01H 5/085; A01H 5/0216; A01H 5/0837; A01H 6/7445; A01H 6/74
See application file for complete search history.

*Primary Examiner* — June Hwu
(74) *Attorney, Agent, or Firm* — Michelle Bos Legal LLC

(57) ABSTRACT

'Vieyra' is a new Rainier-type sweet cherry variety distinguished by its early-maturing fruit.

3 Drawing Sheets

Genus and species: *Prunus avium.*
Variety denomination: 'Vieyra'.

CROSS-REFERENCE TO RELATED APPLICATIONS

None

STATEMENT REGARDING FEDERALLY SPONSORED RESEARCH OR DEVELOPMENT

None

BACKGROUND AND SUMMARY OF THE VARIETY

The new sweet cherry variety 'Vieyra' was discovered by the inventor in 2008, in a 'Rainier' cherry (not patented) orchard near East Wenatchee, Wash. 'Vieyra' is believed to be a whole-tree mutation of 'Rainier', distinguished by its early maturity and larger and redder fruit as compared to 'Rainier'. In 2009, after observing the distinguishing characteristics again, the inventor budded scionwood cuttings of the 'Vieyra' tree on 'Mazzard' rootstock (not patented) near East Wenatchee, Wash., to produce 18 nursery trees for further observation. The test trees were planted in the spring of 2011 near East Wenatchee, with additional test trees planted the following year. 'Vieyra' cherry has been found to exhibit its distinctive characteristics through successive asexually propagated generations.

'Vieyra' was initially selected for, and is distinguished by, its early-maturing fruit. The 'Vieyra' cherry ripens 8 to 10 days earlier than 'Rainier' and exhibits a brighter red overcolor as compared to 'Rainier'. It has also been observed that the trunk lenticels of 'Vieyra' are larger and more prominent than those of 'Rainier'.

As compared to the fruit of the 'Doty' cherry tree (U.S. Plant Pat. No. 13,951) 'Vieyra' cherries are larger, with a brighter overcolor and whiter flesh.

'Vieyra' cherries have a shorter stem and tighter seed cavity than either 'Doty' or 'Rainier' cherries.

BRIEF DESCRIPTION OF THE PHOTOGRAPHS

The accompanying photographs of six-year-old trees of the claimed variety were obtained in 2017 near East Wenatchee, Wash.

Figure 1:
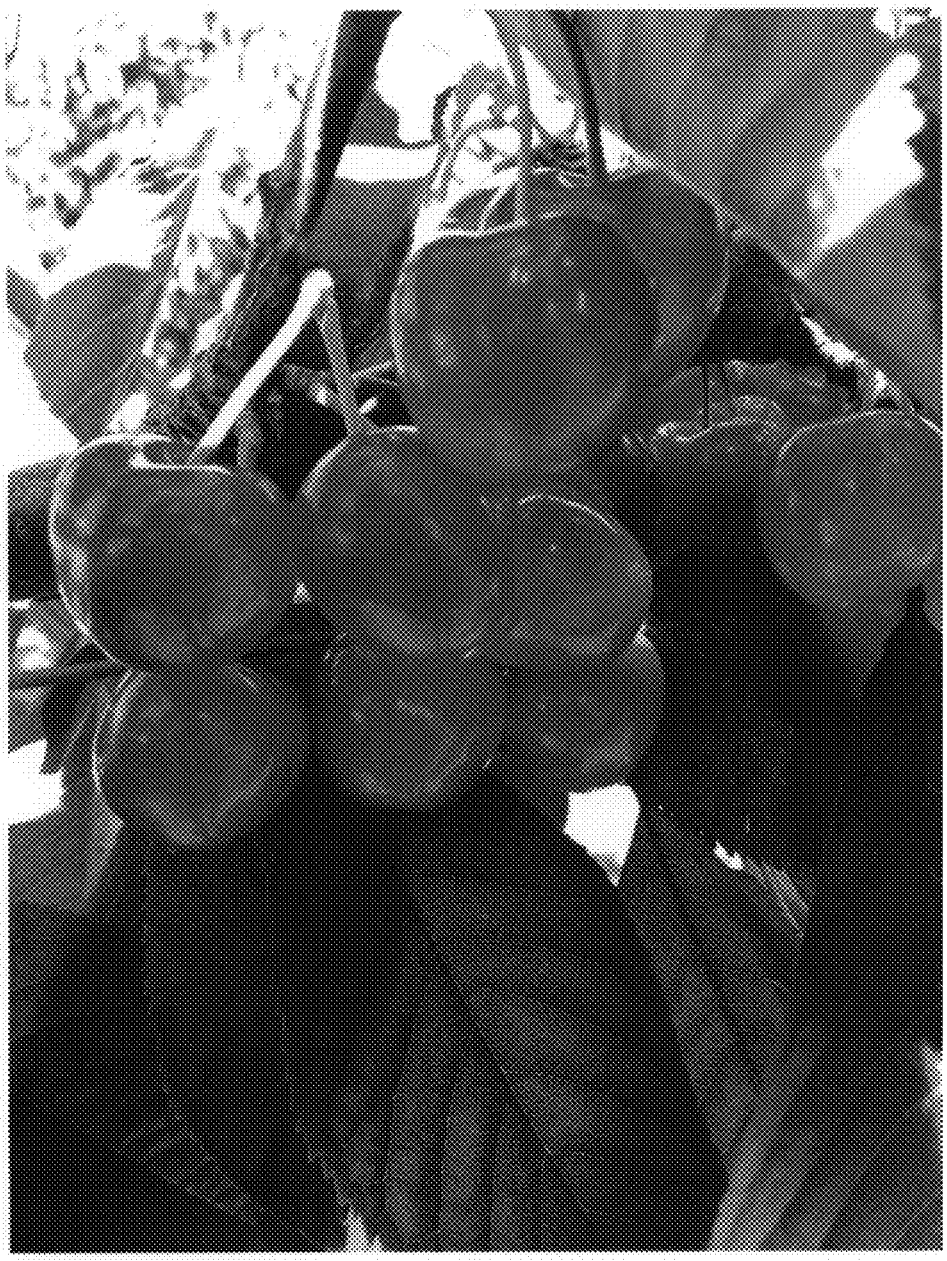
FIG. 1 shows the fruit and leaves of the claimed variety.
Figure 2:
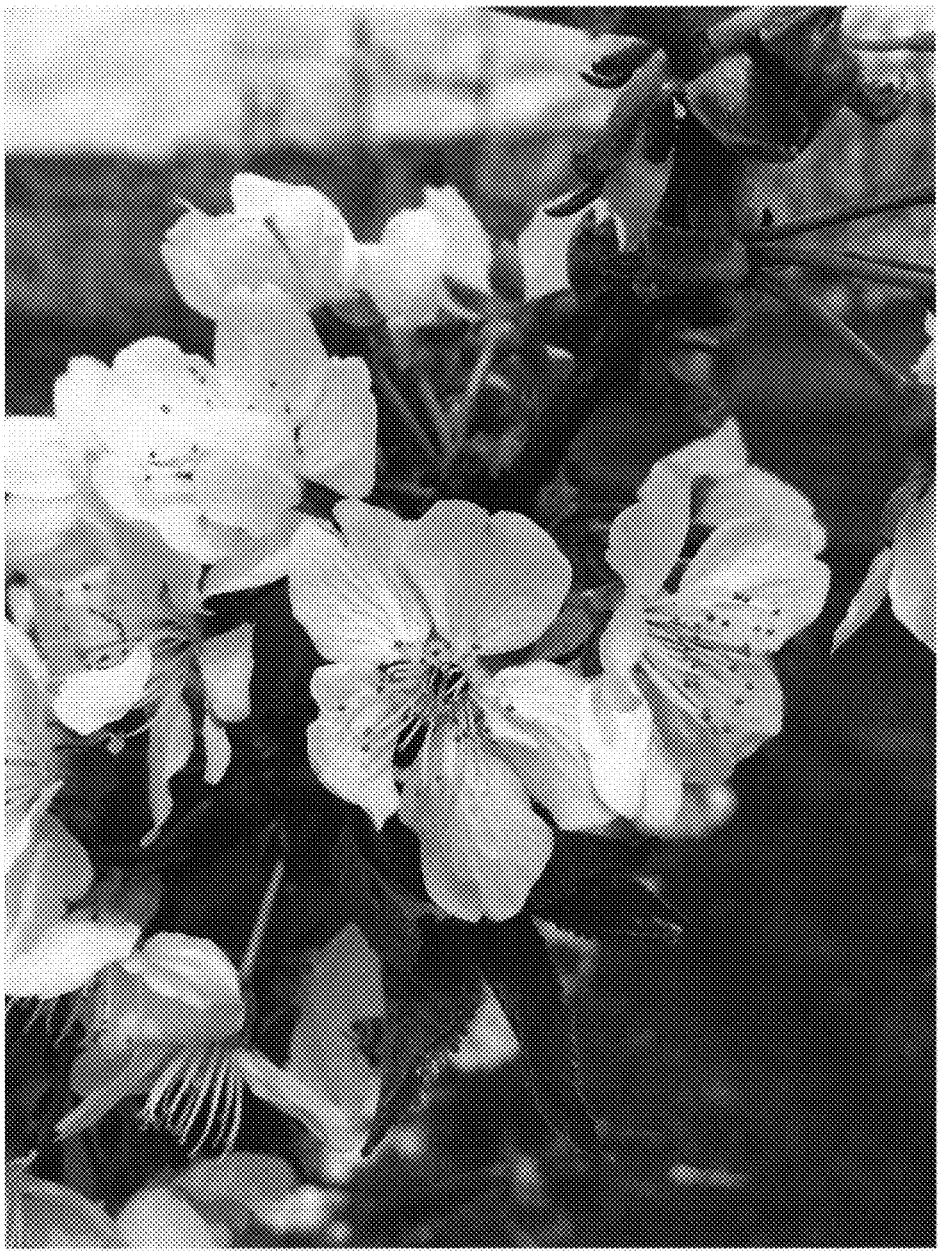
FIG. 2 shows blossoms of the claimed variety.
Figure 3:
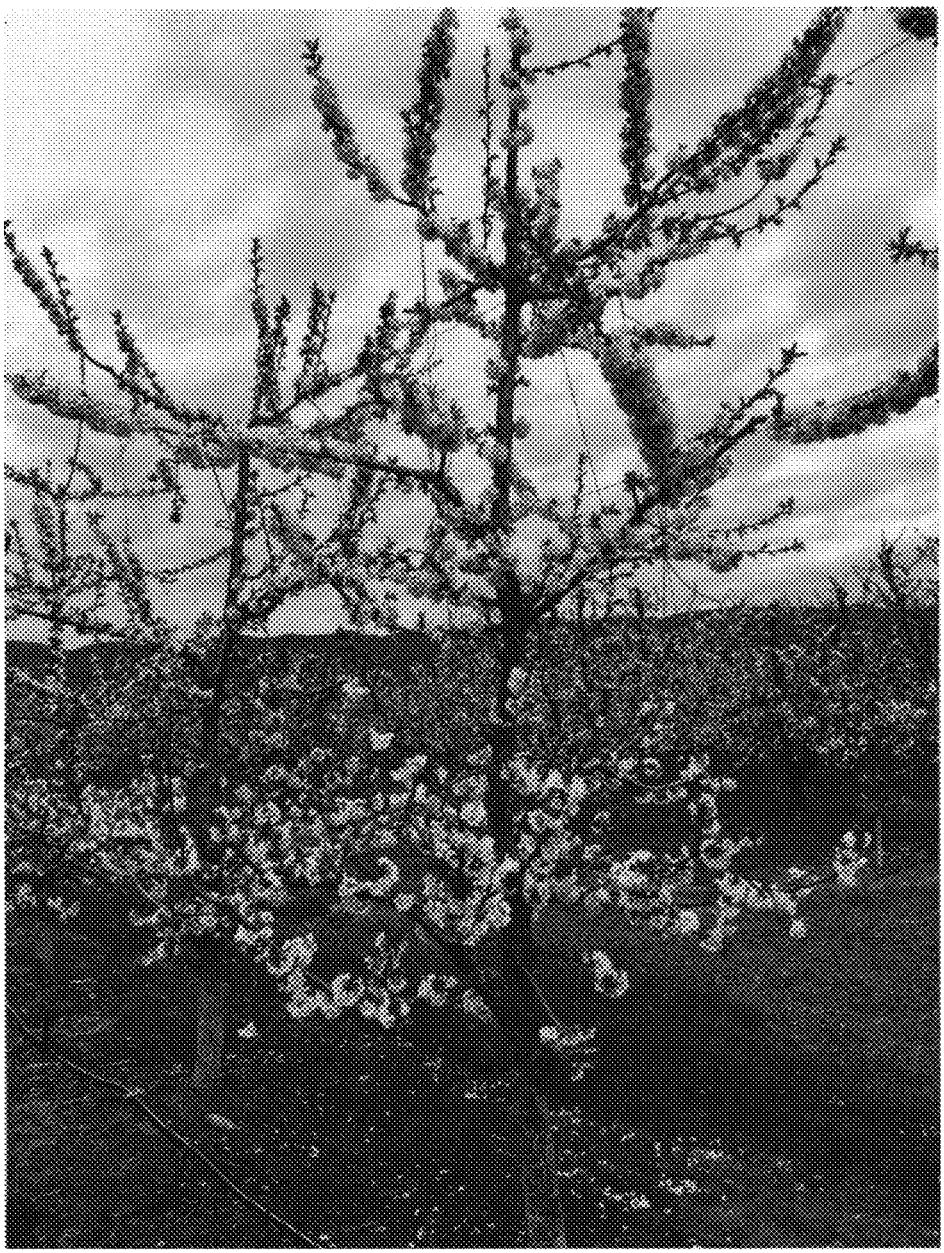
FIG. 3 shows a second generation tree of the variety, in bloom.

The colors of these photographs may vary with lighting conditions. Color characteristics of this new variety should therefore be determined with reference to the observations described herein, rather than from the photographs alone.

DETAILED BOTANICAL DESCRIPTION

The following detailed botanical description is based on observations of second-generation trees of the variety, planted in 2011 and grown on 'Mazzard' rootstock (not patented) on a V-trellis system with 5-foot spacing. Observations were recorded during the 2017 growing season near East Wenatchee, Wash. The characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Colors are described with reference to the Munsell Book of Color.

Tree:

*Vigor.*—Vigorous.
*Habit, shape.*—Columnar.
*Density.*—Moderate, average for sweet cherry trees.
*Height.*—5 m.
*Trunk diameter* (*at* 30 *cm above the graft*).—20 cm.
*Bark texture.*—Smooth with vertical striations and horizontal lenticels.

*Bark coloration.*—7.5 R 2/4 (reddish brown), similar to 'Rainier'.
*Lenticel length.*—1 to 3 cm.
*Lenticel color.*—2.5 R 3/4 (reddish brown).
*Lenticel quantity.*—More numerous than 'Rainier'.

Branch (fruiting branches located at around 1 m above the graft union):
*Diameter.*—40 mm.
*Length.*—About 2 to 3 meters before pruning.
*Crotch angle.*—90°.
*Bark color.*—10 YR 3/2 (medium brown); 10 YR 6/2 (medium tan).
*Bark texture.*—Smooth with prominent lenticels, typical of 'Rainier' and 'Doty'.
*Lenticel length.*—1 to 3 mm.
*Lenticel color.*—10 YR 6/6 (yellowish tan).
*Lenticel quantity.*—Scattered, averaging 1 per $cm^2$.

One year old shoot:
*Length.*—32 to 36 cm.
*Color.*—5 GY 6/6 (light green).
*Pubescence.*—Glabrous.
*Diameter.*—6 mm.
*Internode length.*—3.5 to 5 cm.
*Lenticel length.*—1 mm.
*Lenticel color.*—10 YR 7/2 (grey green).
*Lenticel quantity.*—3 per $cm^2$.

Flower buds:
*Quantity per spur.*—3 to 5.
*Shape.*—Elongate, conic.
*Length.*—15 mm.
*Diameter.*—5 mm.
*Color.*—10 R 3/4 (brown with a reddish tinge).

Flowers:
*Diameter of fully open flower.*—30 to 40 mm.
*Depth of fully open flower.*—25 mm (not including pedicel).
*Relative position of petal margin.*—Overlapping until fully open.
*Pedicel length.*—20 mm.
*Pedicel diameter.*—1.5 mm.
*Pedicel color.*—5 GY 5/10 (medium green).
*Number of flowers per cluster.*—3 to 5.
*Date of first bloom.*—2 days before 'Doty' and 'Santina' (not patented).
*Date of full bloom.*—2 days before 'Doty' and 'Santina'.

Petals:
*Number per flower.*—5.
*Length.*—15 mm.
*Width.*—14 mm.
*Petal shape.*—Round obovate.
*Apex.*—Round.
*Base.*—Acute.
*Margin.*—Smooth with some notching.
*Coloration of upper surface.*—White.
*Coloration of lower surface.*—White.

Pistil:
*Length.*—10 mm.
*Diameter.*—0.5 mm.
*Color.*—2.5 GY 8/8 (pale green).

Stigma:
*Size.*—1 mm.
*Color.*—7.5 Y 8.5/8 (light yellow).

Style:
*Length.*—8 mm.
*Color.*—2.5 GY 6/6 (light green).

Ovary:
*Length.*—1 mm.
*Color.*—2.5 GY 6/6 (light green).

Stamens:
*Quantity.*—Average of 24.
*Anther size.*—0.5 to 1 mm.
*Anther color.*—5Y 6/6 (yellow/brown).
*Filament size.*—Diameter 0.5 mm, length 10 to 15 mm.
*Presence of pollen.*—Abundant.
*Color of pollen.*—7.5 Y 7/10 (yellow).

Sepals:
*Quantity.*—5.
*Color.*—2.5 GY 7/6 (light green).
*Shape.*—Oblong conical.
*Apex.*—Obtuse to acute.
*Base.*—Aequilateral.
*Margin.*—Smooth.
*Length.*—5 mm.
*Width.*—4 mm.

Leaves:
*Length.*—10 to 20 cm, average 18 cm.
*Width.*—6 to 8.5 cm, average 7.5 cm.
*Blade margin.*—Irregularly serrate.
*Leaf shape.*—Obovate.
*Apex shape.*—Acuminate.
*Base shape.*—Oblate to tapering.
*Texture.*—Upper surface smooth; veins pronounced on underside.
*Attitude in relation to shoot.*—Typical of sweet cherries.
*Color of upper surface.*—5 GY 3/4 (dark green).
*Color of lower surface.*—10 GY 4/4 (medium green).

Petiole:
*Length.*—2.5 to 3.5 cm.
*Diameter.*—2 mm.
*Color.*—10 GY 6/6 (medium green).
*Glands.*—2 present. Oblong, 1.5 to 2 mm in length. Bi-colored 10Y 6/6 (grayish yellow green) and 2.5 Y 6/4 (tan), positioned in a groove about 3 cm from base of leaf petiole and about 2 mm below leaf blade.

Fruit:
*Quantity per cluster.*—3 to 5.
*Diameter.*—25 to 30 mm, slightly larger than 'Doty', which runs 25 to 28 mm.
*Length.*—21 to 25 mm.
*Weight.*—Average 1.25 g per fruit, slightly larger than 'Doty', which averages 1.2 g per fruit.
*General shape in profile.*—Reniform
*Shape of pistil end.*—Rounded to slightly indented.
*Depth of stalk cavity.*—3 mm; 1 mm deeper than 'Doty' with more pronounced shoulders.
*Diameter of stalk cavity.*—8 to 12 mm; up to 4 mm wider than 'Doty'.
*Depth of suture.*—Less than 1 mm.
*Skin thickness.*—Thicker than 'Doty'.
*Skin texture.*—Smooth.
*Ground color.*—7.5 Y 8/12 (yellow).
*Overcolor.*—5 R 6/10 (light red) to 5 R 4/14 (dark red).
*Pattern and intensity of overcolor.*—Intense 80% to 90% overcolor, as compared to 70% overcolor on 'Doty'.
*Taste.*—Complex flavor with pleasant bitterness.

Stalk:

*Length.*—28 to 32 mm; shorter than 'Doty'.

*Diameter.*—1.5 mm.

*Color.*—2.5 GY 6/6 (light to medium green).

Flesh:

*Flesh texture.*—Firm and crisp.

*Fibers.*—None detected.

*Aroma.*—Slightly fruitier than 'Doty'.

*Juiciness.*—Juicy.

*Soluble solids.*—19.4 to 20.5° Brix; compare to 16 to 16.8° Brix for 'Doty'.

*Acidity.*—Medium.

*Flesh color.*—5 Y 9/4 (cream).

*Juice color.*—5 Y 9/2 (pale light yellow).

Stone:

*Length.*—10 mm.

*Diameter.*—7 mm.

*Shape.*—Oblong.

*Color.*—2.5 Y 7/8 (brownish yellow).

*Surface texture.*—Smooth.

*Adherence to flesh.*—Semi-freestone.

*Tendency to split.*—Similar to 'Rainier' in area tested.

Harvest:

*Harvest date.*—8 to 10 days before 'Rainier'.

*Number of picks.*—1.

*Productivity per tree.*—20 to 21 kg per tree.

*Bearing.*—Annual.

*Chilling requirement.*—Similar to 'Rainier'.

*Cold hardiness.*—Hardy in area tested (North Central Washington, USDA Zone 5).

Disease resistance/susceptibility: None noted; similar to 'Rainier'.

*Market use.*—Fresh.

*Keeping quality.*—Similar to 'Rainier'.

*Shipping quality.*—Similar to 'Rainier'.

The invention claimed is:

1. A new and distinct variety of cherry tree, substantially as illustrated and described herein.

* * * * *